(12) United States Patent
Ferraiolo

(10) Patent No.: US 10,532,494 B2
(45) Date of Patent: Jan. 14, 2020

(54) GROUND COVERING STRUCTURE AND A PLANT AND A METHOD FOR PRODUCING SAID STRUCTURE

(75) Inventor: Francesco Ferraiolo, Ca' de' Fabbri (IT)

(73) Assignee: OFFICINE MACCAFERRI S.P.A., Zola Predosa (BO) (IT)

( * ) Notice: Subject to any disclaimer, the term of this patent is extended or adjusted under 35 U.S.C. 154(b) by 713 days.

(21) Appl. No.: 13/389,376

(22) PCT Filed: Aug. 13, 2010

(86) PCT No.: PCT/IB2010/053667
§ 371 (c)(1),
(2), (4) Date: Feb. 7, 2012

(87) PCT Pub. No.: WO2011/021137
PCT Pub. Date: Feb. 24, 2011

(65) Prior Publication Data
US 2012/0141214 A1 Jun. 7, 2012

(30) Foreign Application Priority Data
Aug. 20, 2009 (IT) .............................. BO2009A0553

(51) Int. Cl.
*B29B 15/12* (2006.01)
*B32B 5/02* (2006.01)
*B32B 5/26* (2006.01)

(52) U.S. Cl.
CPC ............ *B29B 15/122* (2013.01); *B32B 5/024* (2013.01); *B32B 5/028* (2013.01); *B32B 5/26* (2013.01); *B32B 2305/38* (2013.01)

(58) Field of Classification Search
CPC ............ B32B 5/26; B32B 27/12; B32B 5/022; B32B 2250/20; B32B 5/02; B32B 5/024;
(Continued)

(56) References Cited

U.S. PATENT DOCUMENTS

| 4,012,249 A | 3/1977 | Stapp |
| 4,096,302 A | 6/1978 | Thibodeau et al. |

(Continued)

FOREIGN PATENT DOCUMENTS

| DE | 2 225 043 A1 | 12/1973 |
| IT | 1257665 B | 2/1996 |

(Continued)

OTHER PUBLICATIONS

Office Action of Japan Patent Office issued in Application No. 2012-525237 with English translation dated Jul. 15, 2014 (6 pages).
(Continued)

*Primary Examiner* — Elizabeth C Imani
(74) *Attorney, Agent, or Firm* — Flynn Thiel, P.C.

(57) ABSTRACT

A production plant for a ground covering structure (6) comprises a plant inlet zone and a plant outlet zone for a grid reinforcing member (10). The plant further comprises movement means (4) designed in operation to move the grid reinforcing member (10) along a predetermined path from the inlet zone to the outlet zone, supply means (11) for the supply of plastics material in the fluid state in the form of threads (7) to the reinforcing member (10) disposed along the predetermined path, and cooling means (2, 3) for cooling the plastics material in the form of threads (7) which are tangled on the grid reinforcing structure. The inlet zone and the outlet zone are disposed opposite one another along the predetermined path with respect to the supply means.

9 Claims, 3 Drawing Sheets

(58) Field of Classification Search
CPC ....... B32B 2459/00; B32B 5/028; B32B 5/06; B32B 5/145; B32B 2305/38; B29B 15/122
USPC .......................................................... 442/35
See application file for complete search history.

(56) References Cited

U.S. PATENT DOCUMENTS

| | | | |
|---|---|---|---|
| 4,181,450 A * | 1/1980 | Rasen et al. | ............ 405/19 |
| 4,276,337 A | 6/1981 | Coonrod | |
| 4,340,563 A | 7/1982 | Appel et al. | |
| 5,691,036 A * | 11/1997 | Lin | ........ B32B 5/26 428/172 |
| 5,733,825 A | 3/1998 | Martin et al. | |
| 5,735,640 A | 4/1998 | Meyer et al. | |
| 6,520,237 B1 | 2/2003 | Bolyard, Jr. et al. | |
| 6,875,296 B2 | 4/2005 | Bolyard, Jr. et al. | |
| 7,465,371 B2 * | 12/2008 | Bachmann | ...... B30B 15/061 156/583.1 |
| 2002/0134491 A1 | 9/2002 | Bolyard, Jr. et al. | |
| 2003/0021977 A1 | 1/2003 | Ferraiolo | |
| 2006/0116040 A1 | 6/2006 | Yun et al. | |
| 2013/0105380 A1 | 5/2013 | Ferraiolo | |

FOREIGN PATENT DOCUMENTS

| | | | | |
|---|---|---|---|---|
| JP | 56-167436 A | 12/1981 | | |
| JP | 6-57723 | 3/1994 | | |
| JP | 2002-105881 | 4/2002 | | |
| JP | 2008-542583 | 11/2008 | | |
| WO | WO 2009104003 A1 * | 8/2009 | ............ B32B 5/06 |

OTHER PUBLICATIONS

Form PCT/ISA/220 dated Jun. 10, 2011 (1 page).
Form PCT/ISA/210 dated Jun. 10, 2011 (6 pages).
Form PCT/ISA/237 dated Jun. 10, 2011 and reply thereto dated Nov. 21, 2011 (12 pages).
Form PCT/IPEA/408 dated Jan. 16, 2012 and reply thereto dated Jan. 31, 2012 (8 pages).
Office Action from the Colombian Patent Office issued in Application No. 12-45429-7 dated May 23, 2014 (8 pages).
Office Action of the Eurasian Patent Office with partial English translation dated Jan. 30, 2014 (3 pages).
Documentary Conclusion of Georgian National Intellectual Property Centre dated Apr. 16, 2013 with English translation (5 pages).
Search Report of Georgian National Intellectual Property Centre dated Apr. 16, 2013 with English translation (5 pages).
Examination Report of Korean Patent Office issued in United Arab Emirates Application No. 0164/2012 dated Oct. 31, 2016 (9 pages).

* cited by examiner

GROUND COVERING STRUCTURE AND A PLANT AND A METHOD FOR PRODUCING SAID STRUCTURE

The present invention relates to the sector of ground covering structures.

The invention has been developed with particular reference to a ground covering structure comprising a layer of geocomposite or a plastics material in general and a reinforcing member with a high mechanical strength, for instance of the grid type. The invention also relates to plant and a production method designed particularly for the production of this ground covering structure.

It is known from Italian Patent Specification No 01257665 to cover metal grids with a molten material by means of a production process substantially comprising the depositing of threads of this molten material on a metal grid and the subsequent solidification of the threads by means of a cooling fluid. One of the main drawbacks of the invention set out in Italian Patent Specification No 01257665 is that the threads do not adhere fully to the metal grid and may therefore become detached from this grid during use.

The main object of the present invention is to resolve the drawbacks of known structures by providing a ground covering structure which, for instance, remains whole during its use. A further object of the invention is to provide a ground covering structure which is simple and economic to produce, can be readily installed in safe conditions by operators, and is reliable in use.

In order to achieve the above-mentioned objects, the present invention relates to a ground covering structure and the relative production plant and method as set out in the appended claims.

One of the main advantages of the present invention is that it provides a ground covering structure which is able to retain, efficiently and in a lasting manner, ground areas of small or large dimensions. A further advantage of the invention is that it provides a plant able to use, in operation, a reinforcing member with a high mechanical strength and a high coefficient of rigidity.

Other features and advantages will become clear from the following detailed description of an embodiment of the invention given with reference to the appended drawings which are provided purely by way of non-limiting example and in which.

Figure 1:
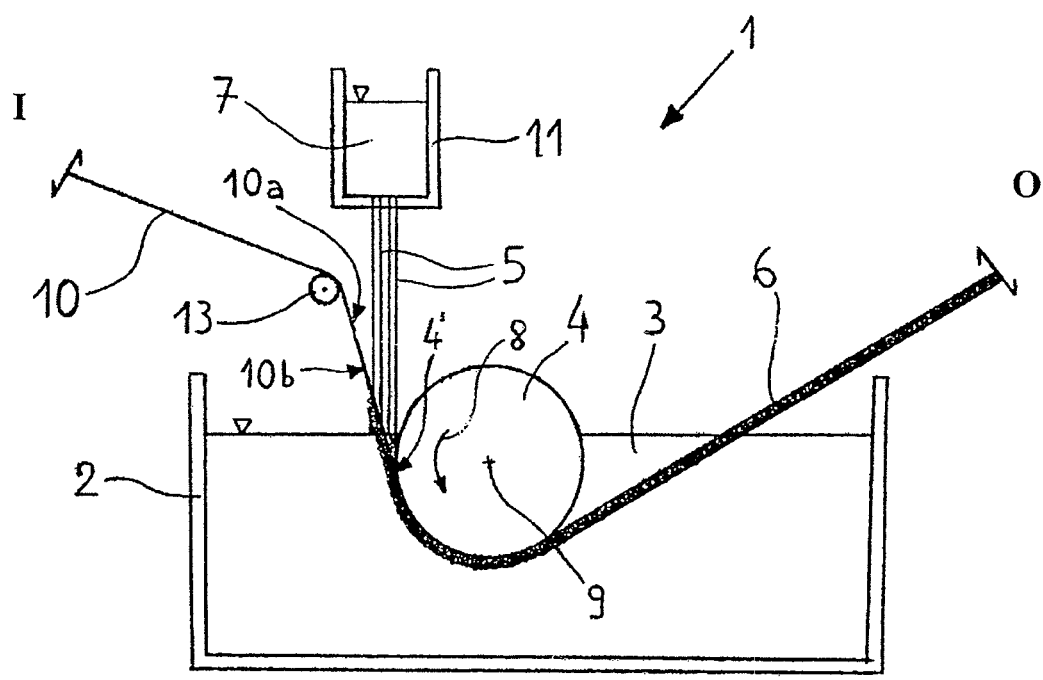
FIG. 1 is a diagram of a plant for the production of a ground covering structure of the present invention.

In FIG. 1, a production plant 1 for a ground covering structure 6 of the present invention comprises an inlet zone "I" through which a reinforcing member 10, preferably of the grid type, for instance, but not exclusively, a metal grid, is inserted into the plant in order to form a reinforcing structure according to the present invention, and an outlet zone "O" from which the ground covering structure 6 is discharged from the plant.

The plant further comprises movement means for moving the reinforcing member 10 from the inlet zone "I" to the outlet zone "O" in a predetermined direction of movement. The movement means preferably comprise a drive member which is preferably, but not exclusively, a roller 4. The roller 4 is connected to motor and/or actuator means (not shown) designed to cause it to rotate about an axis 9, corresponding to its axis of symmetry, in the direction shown by the arrow 8. According to a further embodiment of the present invention, the movement means also comprise a feed reel (not shown) and/or a winder reel (not shown) disposed respectively in the inlet zone and/or in the outlet zone of the plant in order to facilitate the movement of the grid reinforcing member 10 and/or the collection of the finished covering structure 6. The movement means may also comprise one or a plurality of idle rollers 13 disposed upstream and/or downstream of the roller 4 on which the reinforcing member and/or the reinforcing structure may slide in the predetermined direction of movement.

The production plant 1 further comprises means for supplying a plastics material, preferably synthetic polymers and even more preferably a geocomposite material 7 in a fluid state, in the form of threads. The supply means preferably comprise an extrusion unit 11 formed by a container within which the plastics material is brought to its fluid state, and a supply plate disposed on the base of the container. The plate comprises a plurality of holes which may be selectively closed, or a plurality of nozzles or any other supply means through which the plastics material 7 can be supplied in its fluid state in the form of threads. The extrusion unit 11 is disposed in the vicinity of the drive roller 4 and more particularly upstream of the drive roller 4 and downstream of the inlet zone "I" in the predetermined direction of movement or predetermined path of the reinforcing member 10. In this configuration, the inlet zone "I" and the outlet zone "O" are disposed opposite one another in the predetermined direction or predetermined path with respect to the extrusion unit 11.

The plant further comprises cooling means, for instance a tank 2 containing a cooling fluid 3 which is preferably, but not exclusively, water. The tank 2 is elongated in a preferential direction coinciding with the direction or path of movement of the reinforcing member 10 within the plant 1. The drive roller 4 is partially immersed in the cooling fluid 3 and its longitudinal position in the preferential direction or path may be adjusted with respect to the plastics material supply means.

A person skilled in the art could obviously provide different cooling means, for instance devices using air or other cooling devices, without thereby departing from the scope of the invention.

As shown in FIG. 1, the grid reinforcing member 10 comprises a first surface 10a which faces, in use, the drive roller 4 and a second surface 10b opposite the first surface.

The spatial arrangement of the members making up the system of the present invention is particularly designed to achieve the objects and advantages described above. The arrangement in which the inlet zone "I" and the outlet zone "O" are disposed opposite one another in the predetermined direction or path with respect to the supply means 11 means more specifically that the inlet zone "I" and the outlet zone "O" are disposed opposite one another with respect to a vertical plane passing through a tangential line 4' which is defined as the line below the free surface of the cooling water 3 along which the first surface 10a of the reinforcing member 10 comes into contact with the outer surface of the roller 4.

As shown in FIGS. 2 to 5, the reinforcing member 10 preferably, although not exclusively, comprises a metal grid.

This metal grid is more preferably of the double twist type with hexagonal mesh, comprising a plurality of adjacent wires each interwoven with at least one corresponding longitudinal wire 12. The metal wires 12 may preferably, but not exclusively, be made from steel.

The metal grid 10 preferably, but not exclusively, also comprises one or a plurality of metal cables 14, 16, each interwoven or interlinked with at least one adjacent metal wire 12. The metal cables 14, 16 may be disposed in two preferential directions, parallel and at right angles to the direction of the wires 12, and may preferably, but not exclusively, be joined to each other or to the wires 12 by anchoring means 18. The anchoring means 18 may be disposed, for instance, but not exclusively, at each point of intersection of two cables 14, 16 or only at certain points and preferably at the ends of each cable 14, 16. The anchoring means 18 may be distributed in the metal grid 10 in a substantially uniform manner, or may be concentrated in predetermined zones of the metal grid 10 which will, in this case, comprise zones with different surface strengths. The distribution of the cables 14, 16 in the metal grid may also be substantially uniform or non-uniform. It has been observed that it is particularly advantageous, in terms of strength, to dispose the cables 14, 16 in a regularly spaced manner with a spacing in the range of 20 cm to 1.5 m, with preferred spacings of 25, 40, 50 and 100 cm; these values should not, however, be considered to limit the invention in any way.

FIGS. 2 to 5 show, by way of example, some embodiments and relative variants of the reinforcing member according to the present invention. In these embodiments, the presence of the cables 14, 16 increases the coefficient of rigidity of the metal grid making it difficult, although not impossible, to bend the metal grid in the longitudinal and transverse directions in which the cables 14, 16 extend.

Figure 2:
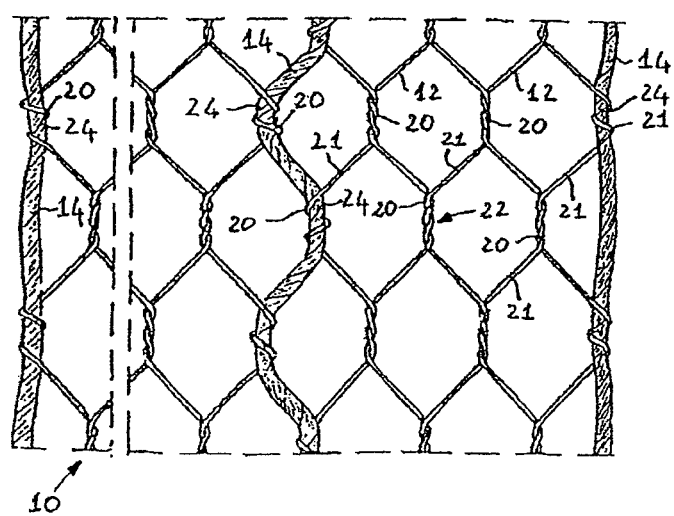
FIG. 2 is a partial plan view of a further embodiment of the metal grid of the present invention.

In FIG. 2, a metal grid 10 comprises a plurality of longitudinal wires 12 adjacent to one another so as to define a longitudinal direction of the metal grid 10. Each wire 12 comprises at least one twisted section 20 and one non-twisted section 21 and is interwoven with at least one other respective longitudinal wire 12, preferably at the location of their respective twisted sections 20. The metal grid 10 further comprises one or a plurality of longitudinal metal cables 14 disposed interwoven with the wires 12. The longitudinal cables 14 may be disposed between two wires 12 or adjacent to one of these wires, for instance at one edge of the metal grid 10. The longitudinal metal cables 14 comprise sections 24 about which twisted sections 20 of one or a plurality of adjacent wires 12 are twisted. According to a further advantageous feature of the present invention, the longitudinal cables 14 may also comprise twisted sections engaged with the longitudinal wires of the metal grid.

Figure 3:
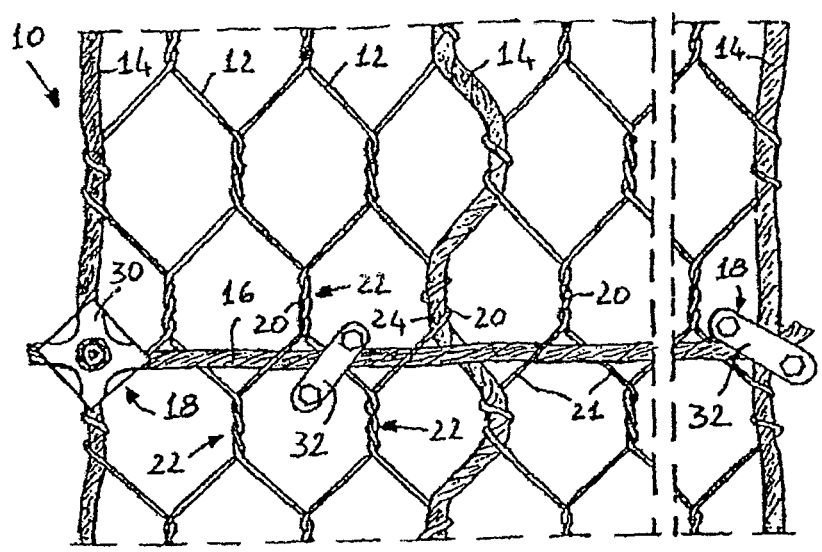
FIG. 3 is a partial plan view of a further embodiment of the metal grid of the present invention.
Figure 5:
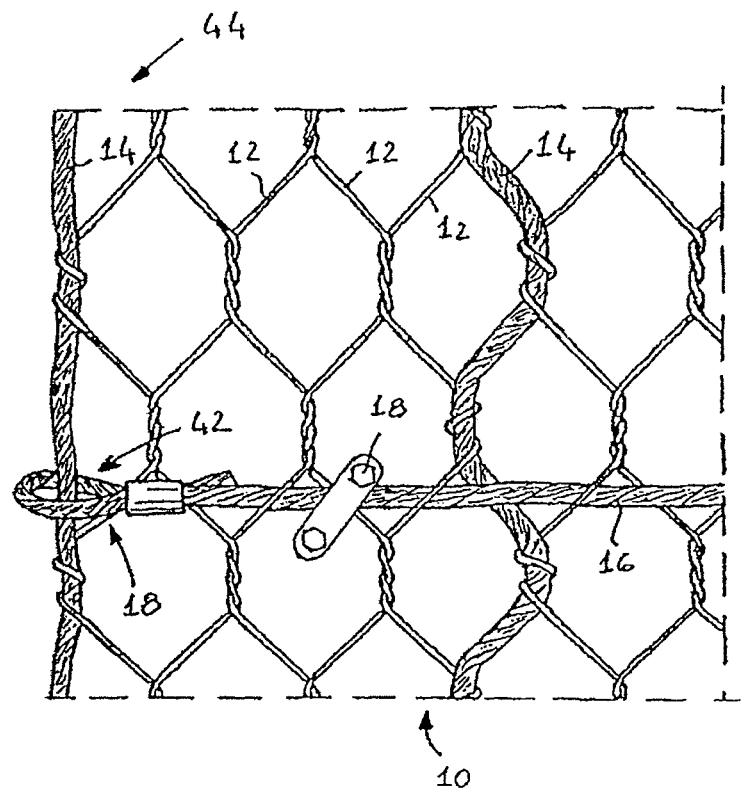
FIG. 5 is a partial plan view of a further variant of the embodiment of FIG. 4.

FIG. 3 shows a further embodiment of the present invention in which a metal grid 10 similar to that shown in FIG. 2 comprises one or a plurality of transverse cables 16 disposed transversely to the longitudinal cables 14. The transverse cables 16 are interwoven over their entire length, or only over part of that length, with the longitudinal wires 12 and/or the longitudinal cables 14 and disposed externally to interwoven zones 22 formed by two twisted sections 20 of wires 12 and/or by the sections 24 of longitudinal cables 14. The anchoring means 18 preferably, but not exclusively, comprise shaped plates 30 or clamps 32 or eyelets 42 obtained directly in the transverse cables 16 or engaged therewith as shown in FIG. 5.

Anchoring means of the same or different types may be used at will in the same metal grid without thereby departing from the scope of the present invention.

Figure 4:
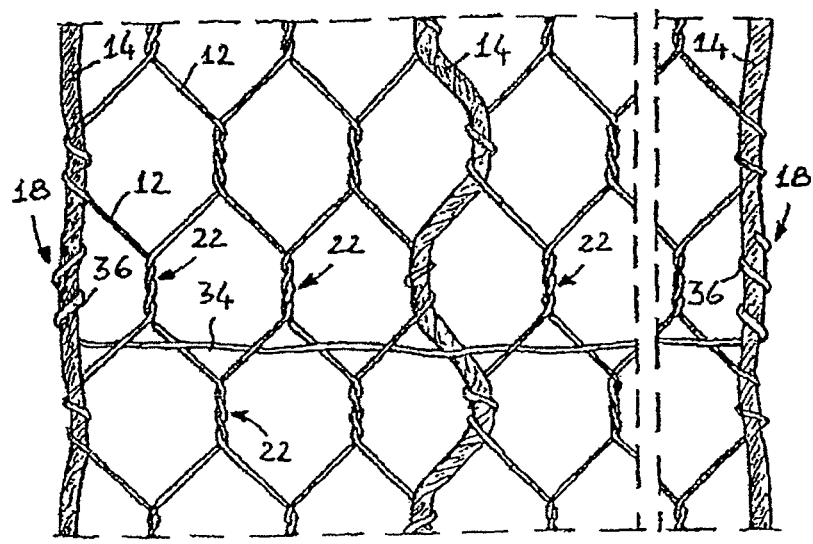
FIG. 4 is a partial plan view of a further embodiment of the metal grid of the present invention.

In one of the further embodiments shown in FIG. 4, the metal grid 10 comprises one or a plurality of transverse wires 34 engaged with the longitudinal wires 12 or the longitudinal cables 14 by means of the anchoring means 18 described above. In this configuration, the anchoring means 18 disposed on the edge of the grid 10 comprise one end 36 of the transverse wires 34 wound about a longitudinal wire 12 or a longitudinal cable 14.

In operation, according to the method of the present invention, a grid reinforcing member, for instance a metal grid 10 as described above, is placed in the inlet zone "I" of the plant 1. The metal grid 10 is then engaged with the movement means until it is wound on a lower portion of the roller 4. The roller 4 is then caused to rotate and, as it rotates, drives the metal grid 10 towards the outlet zone "O", optionally with the assistance of a winder reel disposed downstream of the roller 4. At the same time, the supply means, preferably the extrusion unit 11, start to supply the plastics material 7 in the fluid state contained therein, such that the threads 5 are deposited on the metal grid 10. Advantageously, the reciprocal arrangement of the roller 4 and the extrusion unit 11 may be such that a first proportion of threads 5 comes into contact with the surface of the metal grid 10 before the latter is immersed in the cooling fluid 3, and remains engaged with the mesh of the grid and also projects below the latter in a haphazard manner in the vicinity of the surface 10b. When the portion of metal grid 10 with the threads of plastics material comes into contact with the cooling fluid 3, the threads become tangled and are attached to the mesh of the grid on both the first surface 10a and the second surface 10b.

In this arrangement, a second proportion of threads 5 falls directly into the cooling fluid in a position between the outer surface of the roller 4 and the first surface 10a of the metal grid. This second proportion of threads 5 becomes tangled as the threads fall into the cooling fluid 3 and then engages with the first surface 10a and the threads 5 already present on the metal grid 10. The rotation of the roller then drives the first surface 10a in contact with the outer surface of the roller 4 pressing the second proportion of threads 5 on the first surface 10a. In this way, even if the second proportion of threads 5 tends to harden when it comes into contact with the cooling fluid 3, thereby reducing its ability to engage with and adhere to the grid 10, the pressure action between the grid and the roller 4 makes it possible to overcome this drawback and improve adhesion. Preferably, the peripheral speed of the roller 4 is lower than the speed at which the threads 5 of plastics material emerge from the extrusion unit 11 so that the reinforcing member 10 may be completely covered by the threads 5.

Figure 6:
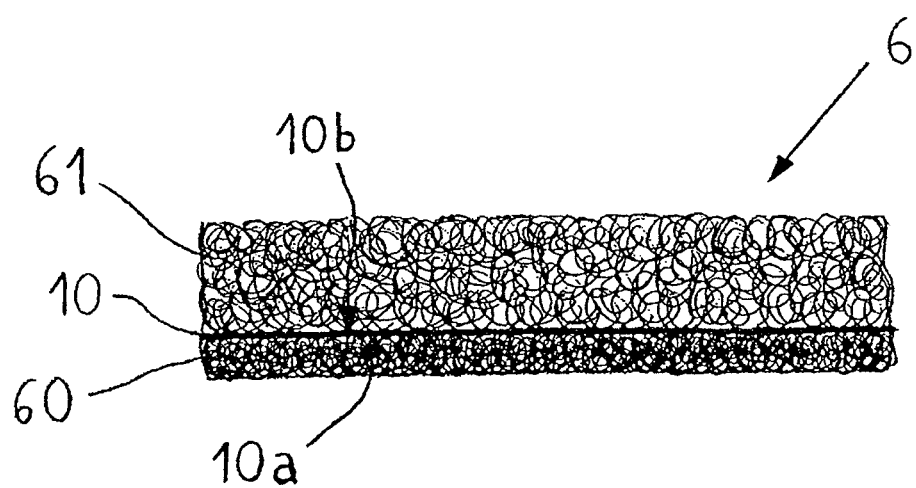
FIG. 6 is a partial view in cross-section of a ground covering structure of the present invention.

On output from the roller 4, a ground covering structure 6, partly shown in detail in FIG. 6, is thus produced and comprises a metal grid 10 completely covered by a layer of geocomposite formed by the tangled threads 5 in the solid state. This covering structure comprises a lower portion 60 and an upper portion 61 respectively facing the first surface 10a and the second surface 10b of the metal grid 10.

According to one of the embodiments of the present invention, following the crushing action of the roller 4, the concentration of threads on the lower portion 60 of the covering structure is substantially denser than the concentration of threads on the upper portion 61. The thicknesses of the layer of geocomposite of the two portions 60, 61 of the covering structure depend on the relationship between the speed at which the threads 5 fall and the speed of rotation of the roller 4. In other words, the grid structure 10 is disposed substantially in an intermediate position with respect to the overall thickness of the finished reinforcing structure, and the plastics wires tangled therewith are denser or more compact on one of the two sides of the grid structure than on the other side.

The tangling of the plastics wires on the grid reinforcing structure, whether substantially uniform or at different densities on the two sides of the grid reinforcing member, makes it possible to retain, effectively and in a lasting manner, ground areas of small or large dimensions.

Naturally, the principle of the invention remaining the same, the embodiments and details of construction may be widely varied with respect to those described and illustrated, without thereby departing from the scope of the present invention.

The invention claimed is:

1. A ground covering structure produced by a production plant comprising:
   a plant inlet zone and a plant outlet zone for a grid type reinforcing member;
   a moving apparatus designed in operation to move the grid type reinforcing member along a predetermined path from the inlet zone to the outlet zone;
   a supply for supplying plastics material in the form of threads in a fluid state, the threads in the fluid state being supplied to the grid type reinforcing member; and
   a cooler for cooling, in operation, the plastics material in the form of threads and thus to form a tangled plastics structure on the grid type reinforcing member;
   wherein the inlet zone and the outlet zone are disposed opposite one another along the predetermined path with respect to the supply;
   wherein the ground covering structure comprises the plastics structure with threads tangled on the grid type reinforcing member disposed in an intermediate position with respect to a thickness of the covering structure, and wherein a substantially uniform concentration of threads on one side of the grid type reinforcing member is substantially denser than a substantially uniform concentration of threads on the other side of the grid type reinforcing member.

2. The ground covering structure according to claim 1, the grid type reinforcing member comprising a plurality of adjacent longitudinal wires each interwoven with at least one respective adjacent longitudinal wire, wherein the grid type reinforcing member further comprises at least one longitudinal metal cable each interwoven or interconnected with at least one of the adjacent longitudinal wires.

3. A method for the production of a ground covering structure comprising the stages of:
   providing a grid type reinforcing member;
   immersing and moving the grid type reinforcing member within a cooling fluid along a predetermined path;
   supplying plastics material in a fluid state in the form of threads to a portion of the grid type reinforcing member immersed in the cooling fluid by a supply;
   pressing the plastics material in the form of threads deposited on the portion of the grid type reinforcing member immersed in the cooling fluid to promote adhesion thereof in a tangled manner to the grid type reinforcing member; and
   removing the portion of the grid type reinforcing member with the plastics material adhering thereto from the cooling fluid.

4. The method according to claim 3, wherein the grid type reinforcing member comprises a grid with a plurality of adjacent longitudinal wires each interwoven with at least one adjacent longitudinal wire, the grid type reinforcing member further comprising at least one longitudinal metal cable each interwoven or interconnected with at least one of the adjacent longitudinal wires.

5. A method for production of the ground covering structure of claim 1, the method comprising:
   providing the grid type reinforcing member;
   immersing and moving the grid type reinforcing member within a cooling fluid along the predetermined path;
   supplying the plastics material in the fluid state in the form of threads to a portion of the grid type reinforcing member immersed in the cooling fluid by the supply;
   pressing the plastics material in the form of threads deposited on the portion of the grid type reinforcing member immersed in the cooling fluid to promote adhesion thereof in a tangled manner to the grid type reinforcing member;
   removing the portion of the grid type reinforcing member with the plastics material adhering thereto from the cooling fluid.

6. The method according to claim 5, wherein the grid type reinforcing member comprises a grid with a plurality of adjacent longitudinal wires each interwoven with at least one adjacent longitudinal wire, the grid type reinforcing member further comprising at least one longitudinal metal cable, the at least one longitudinal metal cable being interwoven or interconnected with at least one adjacent of the longitudinal wires.

7. The method according to claim 3, wherein supplying includes providing a substantially uniform concentration of threads on both sides of the grid type reinforcing member, and pressing results in a substantially uniform concentration of threads on one side of the grid type reinforcing member that is substantially denser than a substantially uniform concentration of threads on the other side of the grid type reinforcing member.

8. The method according to claim 3, wherein the cooling fluid is a liquid.

9. The method according to claim 5, wherein the cooling fluid is a liquid.

* * * * *